United States Patent [19]

Shroff et al.

[11] 4,304,914
[45] Dec. 8, 1981

[54] NAPHTHYRIDONE DERIVATIVES

[75] Inventors: James R. Shroff, Riverside, Conn.; Bernard Loev, Scarsdale, N.Y.

[73] Assignee: USV Pharmaceutical Corporation, Tuckahoe, N.Y.

[21] Appl. No.: 166,424

[22] Filed: Jul. 7, 1980

[51] Int. Cl.³ .......................................... C07D 471/04
[52] U.S. Cl. ................................... 546/123; 546/122; 544/322; 544/328; 544/331; 424/251; 424/256
[58] Field of Search ............... 546/123, 122; 424/256, 424/251; 544/328, 331, 322

[56] References Cited

U.S. PATENT DOCUMENTS 3,555,034 1/1971 Diebold et al. ............... 546/122
3,590,036 6/1971 Lesher et al. ................. 546/123
3,963,736 6/1976 Nakagome et al. ........... 546/123

FOREIGN PATENT DOCUMENTS 2607012 8/1977 Fed. Rep. of Germany .
50-111080 9/1975 Japan .

Primary Examiner—John M. Ford
Assistant Examiner—Natalia Harkaway

[57] ABSTRACT

Compounds of the formula

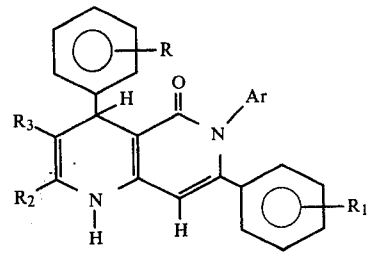

wherein
each of R, $R_1$ and $R_2$ is independently H, alkyl, alkenyl, alkoxy, halo, hydroxy, trifluoromethyl, amino, alkylamino, cyano and nitro;
$R_3$ is carbalkoxy, carboxamide alkanoyl, trifluoromethyl and cyano; and
Ar is heteroaryl or

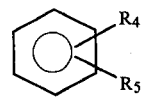

wherein $R_4$ and $R_5$ have the same meaning as each of R, $R_1$ and $R_2$; and acid addition salts thereof have cardiotonic and hypertensive activity.

18 Claims, No Drawings

NAPHTHYRIDONE DERIVATIVES

This invention relates to new pharmaceutically-active compounds and more particularly to certain new cyclic amines possessing useful pharmaceutical activities, especially cardiotonic and anti-hypertensive activity.

The new compounds of this invention are substituted naphthyridones of the formula:

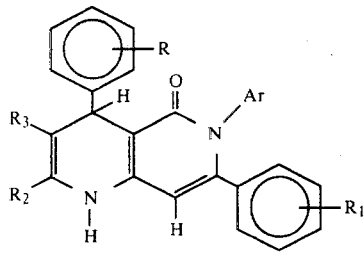

wherein
each of R, $R_1$ and $R_2$ is H, alkyl, alkenyl, alkoxy, halo, hydroxy, trifluoromethyl, amino, alkylamino, cyano and nitro;
$R_3$ is carbalkoxy, carboxamido, alkanoyl, trifluoromethyl and cyano; and
Ar is heteroaryl or

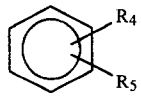

wherein $R_4$ and $R_5$ have the same meaning as each of R, $R_1$ and $R_2$;
and acid addition salts thereof.

The total number of carbon atoms in each such hydrocarbyl substituent is not critical and can range for example up to 10 carbon atoms. The hydrocarbyl radicals can be branched or straight-chained. Preferably, the alkenyl groups and alkyl groups per se and in carbalkoxy, alkylamino, alkoxy and alkanoyl contain up to 7 carbon atoms.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene, and substituted such heterocycles.

The preferred compounds are those in which the hydrocarbyl radicals contain up to about 7 carbon atoms when aliphatic and up to about 10 carbon atoms when aromatic, e.g. phenyl, tosyl and naphthyl.

The most preferred compounds are those in which R is alkoxy or trifluoromethyl, $R_1$ is H, $R_2$ is alkyl, $R_3$ is carbalkoxy and Ar is phenyl or substituted phenyl wherein the substituent is alkoxy or trifluoromethyl.

As should be apparent to those skilled in the art, the present new compounds exist in isomeric forms due to the spatial arrangement of substituents at the 4-position of the cyclic amine, e.g. cis and trans forms. The present new compounds include all of the isomeric forms which can be present in the products as produced by the synthetic process selected for preparation. The mixtures of isomers are useful as are the individual, i.e. separated, isomers for therapy or for conversion one into the other by standard procedures used for such conversions.

The present new compounds are preparable by art-recognized procedures. A particularly effective procedure involves condensation of cyclic amines of the formula:

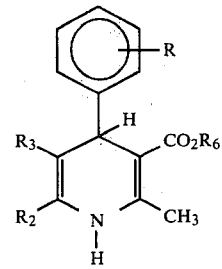

in which R, $R_2$ and $R_3$ are as hereinbefore defined and $R_6$ is lower alkyl, with a benzimidoyl chloride of the formula:

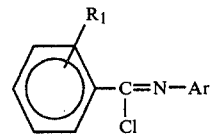

in which $R_1$ and Ar are as previously described. The condensation reaction is usually carried out in a reaction-inert organic solvent, usually a polar solvent which is water-miscible. Suitable solvents are known to those skilled in the art and include dimethylformamide, tetrahydrofuran, dioxane, lower alkanols and similar solvents. The reaction is effected in the presence of an alkali metal hydride or alkoxide. Hydrides are preferred since their use permits visual observation of the alkali metal compound formation with the cyclic amine, i.e. by virtue of hydrogen gas evolution. After alkali metal compound formation, the benzimidoyl chloride is added and the reaction allowed to proceed. Generally, after the initial reaction subsides, the mixture is heated at reflux to assure completeness of the reaction. The product is obtained by standard procedures, as by evaporation of solvent and dissolution of the residue in solvent followed by crystallization.

The starting compounds for the condensation reaction are known compounds or are preparable by art-recognized procedures, e.g. the cyclic amines by the method described in U.S. Pat. No. 3,455,945; German Published Specifications Nos. 2,117,571; 2,117,572 and 2,405,658.

Employing the aforesaid condensation reaction, a variety of new compounds of Formula I can be prepared:

| R | $R_1$ | $R_2$ | $R_3$ | Ar |
|---|---|---|---|---|
| $CH_3$ | H | H | H | $C_6H_5$ |
| $CH_3$ | H | $CH_3$ | H | $C_6H_5$ |
| $CH_3$ | H | H | H | $C_6H_4Cl$ |
| $CH_3$ | H | H | CN | $C_6H_4CH_3$ |
| $C_2H_5$ | H | CN | H | $C_4H_3S$ |
| $CH_3$ | H | H | CN | $C_4H_3O$ |
| $CH_3$ | H | OH | H | $C_5H_4N$ |
| $C_3H_7$ | H | H | $CF_3$ | $C_3H_2NS$ |
| $C_4H_9$ | H | $OCH_3$ | H | $C_6H_5CH_2$ |
| $C_6H_{13}$ | H | COOH | H | $C_6H_5$ |

-continued

| R | R₁ | R₂ | R₃ | Ar |
|---|---|---|---|---|
| i-C₄H₉ | OCH₃ | H | CO₂CH₃ | ClC₆H₄ |
| H | H | OCH₃ | CO₂C₂H₅ | MeOC₆H₄ |
| C₆H₅CH₂ | H | CH₃ | CH₃CO | C₆H₄OH |
| C₆H₁₁ | H | CH₃ | CH₃CO | C₆H₄OH |
| H | H | CH₃ | C₂H₅CO | C₆H₄OH |
| C₆H₅ | H | CH₃ | CONH₂ | C₆H₄OH |
| CF₃ | H | CH₃ | CN | C₆H₄OH |
| CF₃ | Cl | Cl | CONH₂ | C₆H₄OH |
| CF₃ | Cl | CH₃ | CONH₂ | C₆H₄OH |
| CF₃ | Cl | CH₃ | CONH₂ | C₆H₄OH |
| H | OCH₃ | CH₃ | CONHCH₃ | C₆H₄OH |
| H | H | CH₃ | CON(CH₃)₂ | C₆H₄OCH₃ |
| H | H | CH₃ | CO₂C₄H₉ | C₆H₄OCH₃ |
| H | H | H | CO₂C₄H₉ | C₆H₄OCH₃ |
| H | H | H | CO₂CH₃ | C₆H₄OCH₃ |
| H | NH₃ | CH₃ | CONH₂ | C₆H₄OCH₃ |
| H | N(CH₃)₂ | CH₃ | CF₃ | C₆H₄OCH₃ |
| H | H | H | CF₃ | C₆H₄OCH₃ |
| H | H | H | CF₃ | C₆H₄OCH₃ |
| OCH₃ | H | CH₃ | CN | C₆H₄OCH₃ |
| OCH₃ | H | H | CONH₂ | C₆H₃(OH)₂ |
| OCH₃ | H | CN | CONH₂ | C₆H₃(OH)₂ |
| OCH₃ | NO₂ | H | CONH₂ | C₆H₃(OH)₂ |
| OCH₃ | H | OH | CONH₂ | C₆H₄OH |
| OCH₃ | H | CF₃ | CO₂C₂H₅ | C₆H₄OH |
| H | H | OCH₃ | CO₂C₂H₅ | C₆H₄OH |
| H | H | COOH | Co₂C₂H₅ | C₆H₄OH |
| H | OCH₃ | H | CO₂C₂H₅ | C₆H₄OH |
| H | H | OCH₃ | CF₃ | C₆H₄OH |
| H | H | H | CN | C₆H₄OH |
| H | OCH₃ | H | CN | C₆H₄OH |

The present new cyclic amines are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric, sulfuric acids, as well as salts of organic acids such as tartaric, acetic, citric, malic, benzoic, glycolic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds show potent selective cardiotonic activities. In addition, these compounds are also useful as antihypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

Ethyl 1,4,5,6-Tetrahydro-2-methyl-4-(2-trifluoromethylphenyl-5-oxo-6-(2-methoxyphenyl)-7-phenyl-1,6-naphthyridine-3-carboxylate To a slurry of sodium hydride (2.6 g, 55 mmole, 50:50 oil dispersion) in dry DMF (50 mL) under nitrogen atmosphere was added a solution of diethyl 1,4-dihydro-4-(2-trifluoromethylphenyl)-2,6-diemthyl-3,5-pyridine dicarboxylate (19.9 g, 50 mmole) in DMF (150 mL). A gas bubbler was attached and the nitrogen flow discontinued and the mixture was warned in a water bath until bubbling ceased. The system was again placed under nitrogen and a solution of N-(2-methoxyphenyl)-benzimidoyl chloride (12.3 g, 50 mmole) in DMF (200 mL) was added slowly. The reaction mixture was refluxed 18 hrs, allowed to cool and vacuum filtered.

The filtrate was evaporated in vacuo to a brown paste which was extracted with refluxing hexane. The hexane-insoluble residue was triturated with isopropanol and recrystallized from acetonitile to afford a white solid (5.4 g, 19.3%).

EXAMPLE 2

Ethyl 1,4,5,6-Tetrahydro-2-methyl-4-(2-methoxyphenyl)-5-oxo-6,7-diphenyl-1,6-naphthyridine-3-carboxylate This product is obtained using the procedure of Example 1 from diethyl 1,4-dihydro-4-(2-methoxyphenyl)-2,6-dimethyl-3,5-pyridine dicarboxylate and N-phenyl-benzimidoyl chloride (3.1 g, 12.6%).

EXAMPLE 3

Ethyl 1,4,5,6-Tetrahydro-2-methyl-4-(2-trifluoromethylphenyl)-5-oxo-6,7-diphenyl-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-phenylbenzimidoyl chloride (1.8 g, 68%).

EXAMPLE 4

Ethyl 1,4,5,6-Tetrahydro-2-methyl-4-(2-trifluoromethylphenyl)-5-oxo-6-(4-fluorophenyl)-7-phenyl-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(4-fluorophenyl)-benzimidoyl chloride (2.5 g, 9.15%).

EXAMPLE 5

Ethyl 1,4,5,6-Tetrahydro-2-methyl-4-(2-trifluoromethylphenyl)-5-oxo-6-(2-pyridyl)-7-phenyl-1,6-naphthyridine-3-carboxylate This product is obtained using the procedure of Example 1, from diethyl 1,4-dihydro-4-(2-trifluoromethylphenyl)2,6-dimethyl-3,5-pyridine dicarboxylate and N-(2-pyridyl)-benzimidoyl chloride HCl (2.5 g, 9.4%).

EXAMPLE 6

Ethyl 1,4,5,6-Tetrahydro-2-methyl-4-(2-trifluoromethylphenyl)-5-oxo-6-(3,4-dimethoxyphenyl)-7-phenyl-1,6-naphthyridine-3-carboxylate This product is obtained using the procedure of Example 1 from diethyl 1,4-dihydro-4-(2-trifluoromethylphenyl)-2,6-dimethyl 3,5-pyridine dicarboxylate and N-(3,4-dimethoxyphenyl)-benzimidoyl chloride (3.2 g, 10.8%).

EXAMPLE 7

Ethyl 1,4,5,6-Tetrahydro-2-methyl-4-(2-trifluoromethylphenyl)-5-oxo-6-phenyl-7-(2-methoxyphenyl)-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(2-methoxyphenyl)-benzimidoyl chloride (1.0 g, 3.6%).

EXAMPLE 8

Ethyl 1,4,5,6-Tetrahydro-2-methyl-4-(2-trifluoromethylphenyl)-5-oxo-6-(4-methoxyphenyl)-7-phenyl-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(4-methoxyphenyl)-benzimidoyl chloride (3.0 g, 22.4%).

EXAMPLE 9

Ethyl 1,4,5,6-Tetrahydro-2-methyl-4(2-trifluoromethylphenyl)-5-oxo-6-(2-trifluoromethylphenyl)-7-phenyl-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(2-trifluoromethylphenyl)-benzimidoyl chloride (4.7 g, 15.5%).

EXAMPLE 10

Ethyl 1,4,5,6-Tetrahydro-2-methyl-4-(2-trifluoromethylphenyl)-5-oxo-phenyl-7-(2-trifluoromethylphenyl)-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(2-trifluoromethylphenyl)-benzimidoyl chloride (1.8 g, 5.8%).

EXAMPLE 11

Ethyl 1,4,5,6-Tetrahydro-2-methyl-4-(2-trifluoromethylphenyl)-5-oxo-6-(4-trifluoromethylphenyl)-7-phenyl-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(4-trifluoromethylphenyl)-benzimidoyl chloride (1.7 g, 5.6%).

EXAMPLE 12

Ethyl 1,4,5,6-Tetrahydro-2-methyl-4-(2-trifluoromethylphenyl)-5-oxo-6-(3-methoxyphenyl)-7-phenyl-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(3-methoxyphenyl)-benzimidoyl chloride (2.2 g, 8.7%).

EXAMPLE 13

Ethyl 1,4,5,6-Tetrahydro-2-methyl-4-(2-trifluoromethylphenyl)-5-oxo-6,7-di(2-methoxyphenyl)-1,6-naphthyridine-3-carboxylate This product is obtained using the procedure of Example 1 from diethyl 1,4-dihydro-4-(2-trifluoromethylphenyl)-2,6-dimethyl-3,5-pyridine dicarboxylate and N-(2-methoxyphenyl)-2-methoxy-benzimidoyl chloride (1.2 g, 4.1%).

EXAMPLE 14

Ethyl 1,4,5,6-Tetrahydro-2-methyl-4,7-diphenyl-5-oxo-6-(2-methoxyphenyl)-1,6-naphthyridine-3-carboxylate This product is obtained using the procedure of Example 1 from diethyl 1,4-dihydro-4-phenyl-2,6-dimethyl-3,5-pyridine dicarboxylate and N-(2-methoxyphenyl)-benzimidoyl chloride (3.0 g, 12.2%).

What is claimed is:

1. A therapeutically active compound of the formula

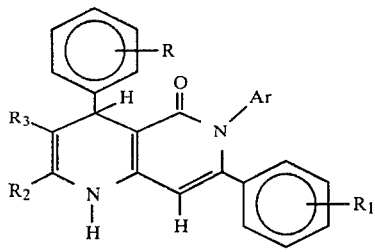

wherein

R and R₁ are independently H, alkyl, alkenyl, alkoxy, halo, hydroxy, trifluoromethyl, amino, alkylamino, cyano or nitro, R₂ is an alkyl or alkenyl containing 1 to 5 carbon atoms, R₃ is H, carbalkoxy, carboxamido, alkanoyl, trifluoromethyl or cyano, and Ar is heteroaryl selected from the group consisting of thiophene, furan, pyridine, thiazole, pyrimidine, pyrrole, benzofuran, quinoline, benzothiophene or a radical of the formula

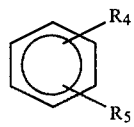

wherein R₄ and R₅ have the same meaning as R and R₁;

wherein the alkenyl groups, the alkyl groups per se and the alkyl groups in alkoxy, alkylamino, carbalkoxy and alkanoyl contain up to 10 carbon atoms; and acid addition salts thereof.

2. A compound according to claim 1 wherein the alkenyl groups and the alkyl groups per se and the alkyl groups in alkoxy, alkylamino, carbalkoxy and alkanoyl contain up to 7 carbon atoms.

3. The compound according to claim 2 wherein R is trifluoromethyl, R₃ is carbalkoxy, R₁ is H, R₂ is alkyl and Ar is phenyl or substituted phenyl wherein the substituent is alkoxy or trifluoromethyl.

4. A compound according to claim 1 of the formula

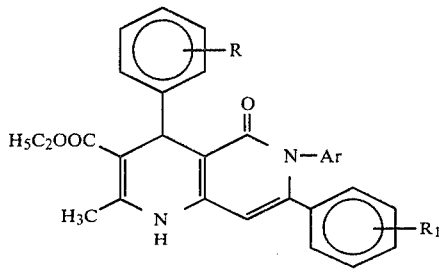

wherein
R, R₁ and Ar are as defined in claim 1.

5. A compound according to claim 4 wherein
R is 2-trifluoromethyl,
R₁ is hydrogen, and
Ar is 2-methoxyphenyl.

6. A compound according to claim 4 wherein
R is 2-methoxy,
R₁ is hydrogen, and
Ar is phenyl.

7. A compound according to claim 4 wherein
R is 2-trifluoromethyl,
R₁ is hydrogen, and
Ar is phenyl.

8. A compound according to claim 4 wherein
R is 2-trifluoromethyl,
R₁ is hydrogen, and
Ar is 4-fluorophenyl.

9. A compound according to claim 4 wherein
R is 2-trifluoromethyl,
R₁ is hydrogen, and
Ar is 2-pyridyl.

10. A compound according to claim 4 wherein
R is 2-trifluoromethyl,
R₁ is hydrogen, and
Ar is 3,4-dimethoxyphenyl.

11. A compound according to claim 4 wherein
R is 2-trifluoromethyl,
R₁ is 2-methoxy, and
Ar is phenyl.

12. A compound according to claim 4 wherein
R is 2-trifluoromethyl,
R₁ is hydrogen, and
Ar is 4-methoxyphenyl.

13. A compound according to claim 4 wherein
R is 2-trifluoromethyl,
R₁ is hydrogen, and
Ar is 2-trifluoromethylphenyl.

14. A compound according to claim 4 wherein
R is 2-trifluoromethyl,
R₁ is hydrogen, and
Ar is 4-trifluoromethylphenyl.

15. A compound according to claim 4 wherein
R is 2-trifluoromethyl,
R₁ is hydrogen, and
Ar is 3-methoxyphenyl.

16. A compound according to claim 4 wherein
R is 2-trifluoromethyl,
R₁ is 2-methoxy, and
Ar is 2-methoxyphenyl.

17. A compound according to claim 4 wherein
R is hydrogen,
R₁ is hydrogen, and
Ar is 2-methoxyphenyl.

18. A hydrochloride salt of the compound according to claim 3.

* * * * *